US00PP35883P2

(12) United States Plant Patent
Arts

(10) Patent No.: US PP35,883 P2
(45) Date of Patent: Jun. 25, 2024

(54) ***MANDEVILLA* PLANT NAMED 'MAN222903'**

(50) Latin Name: *Mandevilla sanderi*
Varietal Denomination: MAN222903

(71) Applicant: MBA B.V., De Kwakel (NL)

(72) Inventor: Niels Arts, Aalsmeer (NL)

(73) Assignee: MBA B.V., De Kwakel (NL)

( * ) Notice: Subject to any disclaimer, the term of this patent is extended or adjusted under 35 U.S.C. 154(b) by 0 days.

(21) Appl. No.: 18/117,685

(22) Filed: Mar. 6, 2023

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
CPC ... A01H 5/02; A01H 5/00; A01H 6/08; A01H 6/088
See application file for complete search history.

(56) References Cited

PUBLICATIONS

*Mandevilla* Breeders Association Summerstar Pink, retrieved on Jun. 29, 2023 at https://mandevillabreeders.com/en/crops/summerstar-pink-2/, one page. (Year: 2023).*
Vellekoop, Preview Flower Trials #2 Floral Daily, retrieved on Jun. 29, 2023 at https://www.floraldaily.com/article/9015174/preview-flowertrials-2/, 13 pp. (Year: 2018).*
YouTube video New variety *Mandevilla* Summerstar collection uploaded 2021 by Agriom, retrieved on Jun. 29, 2023 at https://www.youtube.com/watch?v=c71PFYO2Lu4, 2 pp. (Year: 2021).*

* cited by examiner

*Primary Examiner* — June Hwu
(74) *Attorney, Agent, or Firm* — C. Anne Whealy

(57) ABSTRACT

A new and distinct cultivar of *Mandevilla* plant named 'MAN222903', characterized by its relatively compact, upright to spreading and vining plant habit; vigorous growth habit; glossy dark green-colored leaves; early and freely flowering habit; and purplish red-colored flowers.

2 Drawing Sheets

Figure 1:
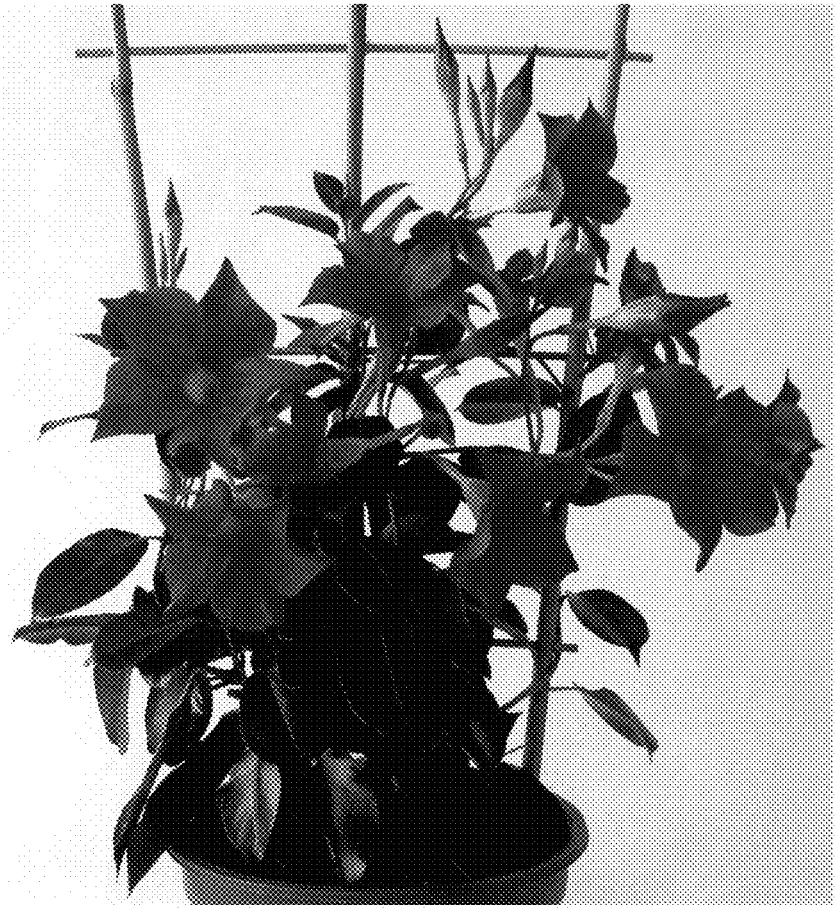

Botanical designation: *Mandevilla sanderi*.
Cultivar denomination: 'MAN222903'.

BACKGROUND OF THE INVENTION

The present invention relates to a new and distinct cultivar of *Mandevilla* plant, botanically known as *Mandevilla sanderi* and hereinafter referred to by the name 'MAN222903'.

The new *Mandevilla* plant is a product of a planned breeding program conducted by the Inventor in De Kwakel, The Netherlands. The objective of the breeding program is to create new freely-flowering *Mandevilla* plants with large attractive flowers and good container performance.

The new *Mandevilla* plant originated from a cross-pollination in De Kwakel, The Netherlands in May, 2015 of *Mandevilla sanderi* 'MAN216901', disclosed in U.S. Plant Pat. No. 29,001, as the female, or seed parent with a proprietary selection of *Mandevilla sanderi* identified as code number 13-0145-046, not patented, as the male, or pollen, parent. The new *Mandevilla* plant was discovered and selected by the Inventor as a single flowering plant from within the progeny of the stated cross-pollination in a controlled greenhouse environment in De Kwakel, The Netherlands in May, 2017.

Asexual reproduction of the new *Mandevilla* plant by vegetative cuttings in a controlled greenhouse environment in De Kwakel, The Netherlands, since August, 2017 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MAN222903'. These characteristics in combination distinguish 'MAN222903' as a new and distinct *Mandevilla* plant:

1. Relatively compact, upright to spreading and vining plant habit.
2. Vigorous growth habit.
3. Glossy dark green-colored leaves.
4. Early and freely flowering habit.
5. Purplish red-colored flowers.

Plants of the new *Mandevilla* can be compared to plants of the female parent, 'MAN216901'. Plants of the new *Mandevilla* differ primarily from plants of 'MAN216901' in flower color as plants of the new *Mandevilla* have purplish red-colored flowers whereas plants of 'MAN216901' have white-colored flowers. In addition, plants of the new *Mandevilla* are more compact than plants of 'MAN216901'.

Plants of the new *Mandevilla* can be compared to plants of the male parent selection. Plants of the new *Mandevilla* differ primarily from plants of male parent selection in plant habit as plants of the new *Mandevilla* are more compact than plants of the male parent selection.

Plants of the new *Mandevilla* can be compared to plants of *Mandevilla sanderi* 'MAN217901', disclosed in U.S. Plant Pat. No. 29,708. In side-by-side comparisons, plants of the new *Mandevilla* differ primarily from plants 'MAN217901' in the following characteristics:

1. Plants of the new *Mandevilla* are more compact than plants of 'MAN217901'.
2. Plants of the new *Mandevilla* grow slower than plants of 'MAN217901'.
3. Plants of the new *Mandevilla* have smaller flowers than plants of 'MAN217901'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of typical flowering plant of 'MAN222903' grown in a container.

Figure 2:
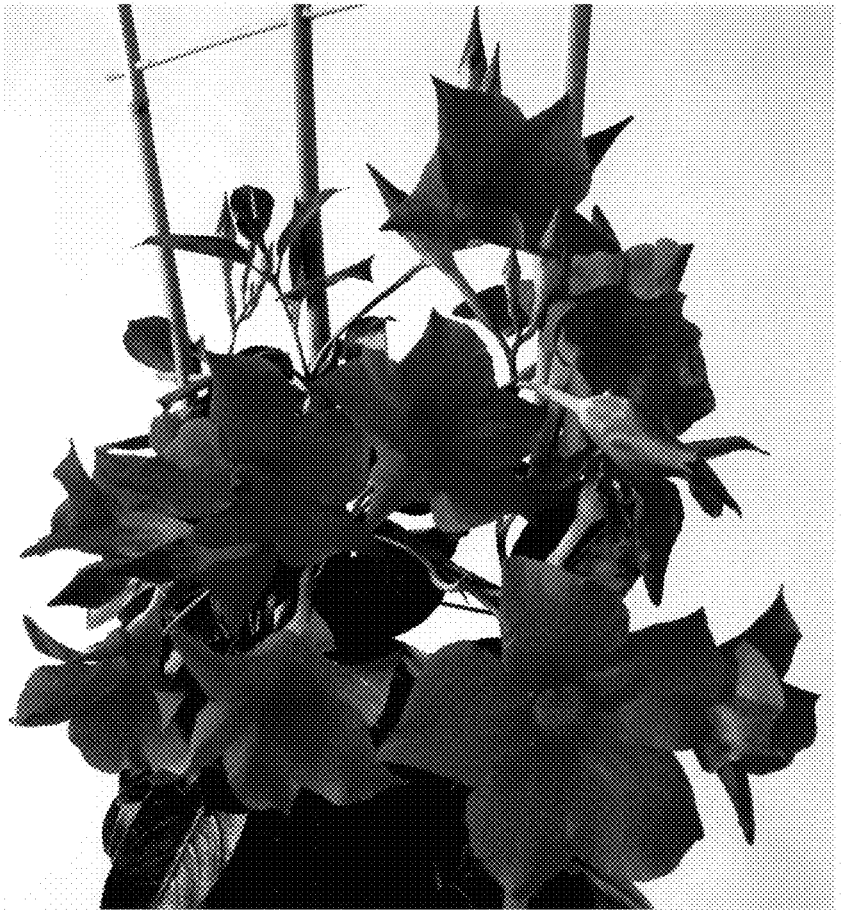

The photograph on the second sheet (FIG. 2) is close-up view of a typical flowering plant of 'MAN222903'.

DETAILED BOTANICAL DESCRIPTION

The aforementioned photographs and following observations, measurements and values describe plants grown during the late spring in 19-cm containers in a glass-covered greenhouse in De Kwakel, The Netherlands and under cultural practices typical of *Mandevilla* commercial production. During the production of the plants, day temperatures ranged from 20 C to 22 C and night temperatures averaged 18 C. Plants were pinched one time four weeks after planting and were twelve months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'MAN222903'.

Parentage:

*Female, or seed, parent.*—*Mandevilla sanderi* 'MAN216901', disclosed in U.S. Plant Pat. No. 29,001.

*Male, or pollen, parent.*—Proprietary selection of *Mandevilla sanderi* identified as code number 13-0145-046, not patented.

Propagation:

*Type.*—By vegetative cuttings.

*Time to initiate roots, summer.*—About 21 days at temperatures about 22 C.

*Time to initiate roots, winter.*—About 27 days at temperatures about 22 C.

*Time to produce a rooted young plant, summer.*—About 40 days at temperatures about 22 C.

*Time to produce a rooted young plant, winter.*—About 50 days at temperatures about 22 C.

*Root description.*—Medium in thickness, fibrous to slightly fleshy; typically white to brownish in color, actual color of the roots is dependent on substrate composition, water quality, fertilizers, substrate temperature and physiological age of roots.

*Rooting habit.*—Freely branching; medium density.

Plant description:

*Plant and growth habit.*—Relatively compact, upright to spreading and vining plant habit; dense and bushy appearance; vigorous growth habit and relatively slow growth rate.

*Plant height.*—About 30 cm.

*Plant diameter (spread).*—About 40 cm.

*Lateral branch description.*—Branching habit: Moderate to freely branching habit with about three primary branches, each primary branch with about three to five secondary lateral branches; pinching enhances lateral branch development. Length, primary branches: About 20 cm to 30 cm. Diameter, primary branches: About 3 mm to 5 mm. Internode length: About 2 cm to 3 cm. Strength: Firm. Aspect: Variable, if not on a trellis, about 30 to 90 degrees from vertical; plants vining. Texture and luster: Smooth, glabrous; semi-glossy becoming woody and matte with development. Color, developing: Close to 144A. Color, developed: Close to 152B; when woody, close to N199C.

Leaf description:

*Arrangement.*—Opposite, simple.

*Length, fully expanded leaves.*—About 5 cm to 7 cm.

*Width, fully expanded leaves.*—About 3.5 cm to 4 cm.

*Shape.*—Ovate.

*Apex.*—Cuspidate.

*Base.*—Obtuse.

*Margin.*—Entire.

*Texture and luster, upper and lower surfaces.*—Smooth, glabrous; leathery; glossy.

*Venation pattern.*—Pinnate.

*Color.*—Developing leaves, upper surface: Close to 137B. Developing leaves, lower surface: Close to 146C. Full expanded leaves, upper surface: Close to 147A and 139A; venation, close to 143C. Fully expanded leaves, lower surface: Close to 146A; venation, close to 146C.

*Petioles.*—Length: About 1 cm to 2 cm. Diameter: About 2 mm. Strength: Strong. Texture and luster, upper and lower surfaces: Smooth, glabrous; glossy. Color, upper surface: Close to 143C. Color, lower surface: Close to 146C.

Flower description:

*Flower type and flowering habit.*—Single salverform flowers arranged in axillary racemes; flowers star-shaped and face upright to mostly outwardly; freely flowering habit with about seven to eight flowers per inflorescence and during the flowering season, about 45 flowers develop per plant.

*Natural flowering season.*—Plants flower continuously from the late spring until the late summer in The Netherlands; early flowering habit, plants begin flowering about seven months after planting.

*Flower longevity on the plant.*—About eight to ten days; flowers not persistent.

*Fragrance.*—None detected.

*Inflorescence height.*—About 10 cm to 12 cm.

*Inflorescence diameter.*—About 10 cm to 15 cm.

*Flower buds.*—Length: About 7.5 cm. Diameter: About 1.2 cm. Shape: Elongated, spindle-shaped. Texture and luster: Smooth, glabrous; semi-glossy. Color: Distally, close to 63A and proximally, close to 145B.

*Flowers.*—Appearance: Flared trumpet, corolla fused and five-parted. Diameter: About 5 cm to 7 cm.

Length: About 6 cm. Throat diameter: About 1.5 cm. Tube length: About 4 cm to 4.5 cm. Tube diameter, proximally: About 4 mm.

*Corolla*.—Quantity and arrangement: Five petals arranged in a single whorl; proximal portion of the petals are fused into a tube; distal free portions slightly imbricate. Petal length: About 3 cm to 3.5 cm. Petal width: About 2.5 cm to 3 cm. Petal shape and appearance: Ovate to triangular, asymmetrical. Petal apex: Acute to cuspidate. Petal margin: Entire; slightly undulate. Petal texture and luster, upper and lower surfaces: Smooth, glabrous; semi-glossy. Throat and tube texture: Smooth, glabrous; semi-glossy. Color: Petal, when opening, upper surface: Close to N57A. Petal, when opening, lower surface: Initially, close to 145D and becoming closer to N57A with development. Petals, fully opened, upper surface: Close to N57A; venation, close to N57A; color does not change with subsequent development. Petal, fully opened, lower surface: Close to 53D; venation, close to 53D; color does not change with subsequent development. Throat: Close to 26A; venation, close to 26A. Tube: Close to 145D and towards the base, close to N57D; venation, close to 145D and N57D.

*Calyx*.—Quantity and arrangement: Five sepals arranged in a single whorl; calyx, star-shaped. Length: About 8 mm. Diameter: About 5 mm. Sepal length: About 6 mm to 7 mm. Sepal width: About 2 mm. Sepal shape: Subulate. Sepal apex: Acute. Sepal margin: Entire. Sepal texture and luster, upper and lower surfaces: Smooth, glabrous; semi-glossy. Sepal color: When opening, upper and lower surfaces: Close to 144C and towards the apex, close to 181B. Fully opened, upper and lower surfaces: Close to 144C and towards the apex, close to 181B.

*Peduncles*.—Length: About 2 cm to 5 cm. Diameter: About 2 mm to 3 mm. Strength: Strong. Aspect: Mostly upright. Texture and luster: Smooth, glabrous; glossy. Color: Close to 144C.

*Pedicels*.—Length: About 1 cm to 2 cm. Diameter: About 2 mm. Strength: Strong. Aspect: Upright to about 30 degrees from peduncle axis. Texture and luster: Smooth, glabrous; glossy. Color: Close to 144C.

*Reproductive organs*.—Stamens: Quantity and arrangement: Typically five; basifixed; anthers connate. Filament color: Close to 14D. Anther length: About 8 mm. Anther shape: Elliptic. Anther color: Close to 18A. Pollen amount: Moderate. Pollen color: Close to 155D. Pistils: Quantity: Typically one. Pistil length: About 2.5 cm. Style color: Close to 145C. Stigma diameter: About 2 mm. Stigma shape: Club-shaped. Stigma color: Close to 144C. Ovary color: Close to 144B.

*Fruits and seeds*.—To date, fruit and seed development have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 1 C to about 45 C.

It is claimed:

1. A new and distinct *Mandevilla* plant named 'MAN222903' as illustrated and described.

* * * * *